United States Patent
Immel (10) Patent No.: US 12,407,945 B2
(45) Date of Patent: Sep. 2, 2025

(54) VIDEO OVERLAY SYNCHRONIZATION FOR A DIGITAL SURGICAL STEREOSCOPE

(71) Applicant: Digital Surgery Systems, Inc., Goleta, CA (US)

(72) Inventor: David S. Immel, Goleta, CA (US)

(73) Assignee: Digital Surgery Systems, Inc., Goleta, CA (US)

( * ) Notice: Subject to any disclaimer, the term of this patent is extended or adjusted under 35 U.S.C. 154(b) by 407 days.

(21) Appl. No.: 17/967,413

(22) Filed: Oct. 17, 2022

(65) Prior Publication Data

US 2023/0117586 A1    Apr. 20, 2023

Related U.S. Application Data (60) Provisional application No. 63/256,475, filed on Oct. 15, 2021.

(51) Int. Cl.
*G06K 9/00* (2022.01)
*A61B 5/02* (2006.01)
(Continued)

(52) U.S. Cl.
CPC ......... *H04N 23/951* (2023.01); *G06T 7/0012* (2013.01); *G06T 2207/10* (2013.01);
(Continued)

(58) Field of Classification Search
CPC ........ G06K 9/00; H04N 5/232; A61B 1/0638; A61B 5/02
USPC ........ 382/100, 106–107, 128–133, 153, 158, 382/162, 168, 173, 181, 189, 191, 199, 382/224, 254, 274, 285–291, 305, 312; 600/310, 321, 329
See application file for complete search history.

(56) References Cited

U.S. PATENT DOCUMENTS

2016/0246041 A1 *  8/2016  Rappel ................... G02B 21/22
2019/0125457 A1 *  5/2019  Parihar .............. A61B 17/0206
(Continued)

OTHER PUBLICATIONS

GradientWhat is the gradient of a scalar function of a symmetric matrix? Shriram Srinivasan—Nishant Panda / Accepted: Aug. 4, 2022 / Published online: Aug. 15, 2022s (Year: 2022).*

*Primary Examiner* — Seyed H Azarian
(74) *Attorney, Agent, or Firm* — K&L Gates LLP; Dennis A. Majewski (57) ABSTRACT

Video overlay synchronization for a digital surgical stereoscope is disclosed herein. In an example, a system provides synchronization by detecting how an image changes between frames. The image change corresponds to detecting the regular and predictable movement of human tissue, such as pulsing of a blood vessel. Peaks or maximum extents of tissue movement is tracked overtime to determine an estimation of the regular periodic movement. This periodic movement is used to align a short recording of images corresponding to a fluorescence imaging mode with a live or near-live recording of images in a visible light mode. The frame rate of fluorescence image data is adjusted to ensure close or almost exact alignment of tissue position shown in both the fluorescence image data and visible light image data. The system accordingly provides a fluorescence image overlay on visible light images for tissue that has regular movement patterns.

20 Claims, 9 Drawing Sheets
(8 of 9 Drawing Sheet(s) Filed in Color)

(51) Int. Cl.
  *G06T 7/00* (2017.01)
  *H04N 5/232* (2006.01)
  *H04N 23/951* (2023.01)

(52) U.S. Cl.
  CPC ............... *G06T 2207/10012* (2013.01); *G06T 2207/10064* (2013.01); *G06T 2207/30101* (2013.01)

(56) References Cited

U.S. PATENT DOCUMENTS

| | | | | |
|---|---|---|---|---|
| 2019/0182415 A1* | 6/2019 | Sivan | ...................... | G06F 3/013 |
| 2019/0320875 A1* | 10/2019 | Jones | .................... | G06T 7/0012 |
| 2020/0093357 A1* | 3/2020 | Scott | .................... | A61B 1/0638 |
| 2021/0109349 A1* | 4/2021 | Schneider | .............. | A61B 90/37 |
| 2021/0386290 A1* | 12/2021 | Yoshida | ............... | A61B 5/0261 |
| 2022/0008158 A1* | 1/2022 | Tripathi | ................ | G06T 19/006 |

\* cited by examiner

VIDEO OVERLAY SYNCHRONIZATION FOR A DIGITAL SURGICAL STEREOSCOPE

PRIORITY CLAIM

This application claims priority to and the benefit as a non-provisional application of U.S. Provisional Patent Application No. 63/256,475, filed Oct. 15, 2021, the entire contents of which are hereby incorporated by reference and relied upon.

CROSS-REFERENCE TO RELATED APPLICATIONS

This application incorporates by reference and relies upon the specification, claims, and drawings of U.S. Provisional Patent Application No. 63/256,468, filed Oct. 15, 2021.

BACKGROUND

Some known surgical camera systems have a fluorescence feature that highlights certain human tissue that emits light in a fluorescence emission spectrum when exposed to fluorescence excitation light. The target human tissue may include a contrast agent such that the tissue (e.g., cancerous tissue or blood vessels) emits fluorescence light while other tissue does not emit fluorescence light. This fluorescence feature enables surgeons to more accurately determine the bounds of cancerous or other tissue for removal or repair. A problem with fluorescence imaging is that image contrast is reduced and healthy tissue is not readily visible. This can be especially problematic for stereoscopic images.

To improve tissue visibility and contrast, some known surgical camera systems overlay image data shown in a visible light spectrum with fluorescence image data shown in an enhanced fluorescence spectrum. Oftentimes, image sensors record alternating visible light image data and fluorescence image data. The alternating image data is combined together such that the fluorescence image data is enhanced for human viewing, made partially transparent, and overlaid on the visible image data. The overlay provides the advantages of visible light by showing healthy tissue and contrast while also highlighting tissue that emits fluorescence light.

This overlay technique works well when tissue is relatively immobile since the positon of the tissue does not change between fluorescence image data and visible light image data. However, this technique does not work when tissue moves. For example, blood vessels, the heart, and lungs move regularly over heartbeat or respiratory cycles. When fluorescence image data is overlaid on visible image data, tissue movement between frames results in the fluorescence image data being offset or misaligned from the visible light data. As a result, this ghost effect prevents users from using this overlay fluorescence feature for regularly moving tissue.

SUMMARY

An apparatus, method, and system are disclosed that provide synchronization between fluorescence image data and visible light image data for tissue that moves with known regularity. The example apparatus, method, and system are configured to provide synchronization by detecting how an image changes between frames. The image change corresponds to detecting the regular and predictable movement of human tissue, such as pulsing of a blood vessel. In particular, peaks or maximum extents of tissue movement is tracked overtime to determine an estimation of the regular periodic movement.

Additionally, the apparatus, method, and system are configured to record a defined time duration of image data in a fluorescence imaging mode. The time duration is defined to include at least two peaks or maximum extents of tissue movement. The example apparatus, method, and system then overlay the recorded fluorescence image data over the live visible light image data such that the peaks or tissue movement extents of the fluorescence image data are aligned with detected peaks or movement extents of the live visible light image data. The frame rate of the fluorescence image data is adjusted to ensure close or almost exact alignment of tissue position shown in both the fluorescence image data and the visible light image data. The example apparatus, method, and system accordingly provide a fluorescence image overlay on visible light images for tissue that has regular movement patterns.

In light of the disclosure set forth herein, and without limiting the disclosure in any way, in a first aspect of the present disclosure, which may be combined with any other aspect, or portion thereof, described herein a surgical imaging apparatus is configured to receive fluorescence image data of patient tissue from a camera. The fluorescence image data has a specified duration. The surgical imaging apparatus is also configured to determine first scalar gradients between subsequent frames of the fluorescence image data, and determine, as recorded fluorescence frames, peak times and a recording start time of the fluorescence image data using the determined scalar gradients plotted over a recording time. The surgical imaging apparatus is further configured to receive live visible light image data, determine second scalar gradients between subsequent frames of the visible light image data, determine, as an overlay time, a time since a last peak of the visible light image data using the determined second scalar gradients, and locate a frame of the recorded fluorescence frames that has the same overlay time since a first recorded peak. The surgical imaging apparatus is additionally configured to create an overlay image by overlaying or superimposing at least a portion of the located frame of the recorded fluorescence frames on the corresponding frame of the visible light image data and cause the overlay image to be displayed.

In a second aspect of the present disclosure, which may be combined with any other aspect, or portion thereof, described herein, the apparatus is further configured to compute a running average time between peaks in the live visible light image data, and adjust a recording frame rate of the recorded fluorescence frames so that a next recorded peak matches a next live peak.

In a third aspect of the present disclosure, which may be combined with any other aspect, or portion thereof, described herein, the apparatus is further configured to at an end of the recorded fluorescence frames, re-compute the starting frame shift and replay the recorded fluorescence frames.

In a fourth aspect of the present disclosure, which may be combined with any other aspect, or portion thereof, described herein, the specified duration is between ten and thirty seconds.

In a fifth aspect of the present disclosure, which may be combined with any other aspect, or portion thereof, described herein, the specified duration includes at least two movement peaks of human tissue.

In a sixth aspect of the present disclosure, which may be combined with any other aspect, or portion thereof, described herein, the fluorescence image data and the visible light image data include stereoscopic image data.

In a seventh aspect of the present disclosure, which may be combined with any other aspect, or portion thereof, described herein, the patient tissue includes at least one of blood vessels, a heart, or lung tissue.

In an eighth aspect of the present disclosure, which may be combined with any other aspect, or portion thereof, described herein, the first scalar gradients are determined by creating a difference image between the subsequent frames of the fluorescence image data, and summing values of the pixels of the difference image.

In a ninth aspect of the present disclosure, which may be combined with any other aspect, or portion thereof, described herein, the subsequent frames are scaled down by at least a factor of four before the difference image is created.

In a tenth aspect of the present disclosure, which may be combined with any other aspect, or portion thereof, described herein, the second scalar gradients are determined by creating a difference image between the subsequent frames of the visible light image data, and summing values of the pixels of the difference image.

In an eleventh aspect of the present disclosure, which may be combined with any other aspect, or portion thereof, described herein, the apparatus is further configured to detect or receive an indication of camera movement, receive new fluorescence image data of the patient tissue from the camera, the new fluorescence image data having the specified duration, responsive to detecting or receiving the indication of the camera movement, determine new first scalar gradients between subsequent frames of the new fluorescence image data, locate a new frame of the new recorded fluorescence frames that has the same overlay time since a new first recorded peak, create a new overlay image by overlaying or superimposing at least a portion of the new located frame of the new recorded fluorescence frames on the corresponding frame of newly received visible light image data, and cause the new overlay image to be displayed.

In a twelfth aspect of the present disclosure, which may be combined with any other aspect, or portion thereof, described herein, a surgical imaging method includes receiving, in a processor, fluorescence image data of patient tissue from a camera. The fluorescence image data has a specified duration. The method also includes determining, via the processor, first scalar gradients between subsequent frames of the fluorescence image data and determining, via the processor as recorded fluorescence frames, peak times and a recording start time of the fluorescence image data using the determined scalar gradients plotted over a recording time. The method further includes receiving, in the processor, live visible light image data, determining, via the processor, second scalar gradients between subsequent frames of the visible light image data, determining, via the processor as an overlay time, a time since a last peak of the visible light image data using the determined second scalar gradients, and locating, via the processor, a frame of the recorded fluorescence frames that has the same overlay time since a first recorded peak. The method additionally includes creating, via the processor, an overlay image by overlaying or superimposing at least a portion of the located frame of the recorded fluorescence frames on the corresponding frame of the visible light image data, and causing, via the processor, the overlay image to be displayed.

In a thirteenth aspect of the present disclosure, which may be combined with any other aspect, or portion thereof, described herein, the method further includes detecting or receiving, in the processor, an indication of camera movement, receiving, in the processor, new fluorescence image data of the patient tissue from the camera, the new fluorescence image data having the specified duration, responsive to detecting or receiving the indication of the camera movement, determining, via the processor, new first scalar gradients between subsequent frames of the new fluorescence image data, locating, via the processor, a new frame of the new recorded fluorescence frames that has the same overlay time since a new first recorded peak, creating, via the processor, a new overlay image by overlaying or superimposing at least a portion of the new located frame of the new recorded fluorescence frames on the corresponding frame of newly received visible light image data, and causing, via the processor, the new overlay image to be displayed.

In a fourteenth aspect of the present disclosure, which may be combined with any other aspect, or portion thereof, described herein, the method further includes computing, via the processor, a running average time between peaks in the live visible light image data, and adjusting, via the processor, a recording frame rate of the recorded fluorescence frames so that a next recorded peak matches a next live peak.

In a fifteenth aspect of the present disclosure, which may be combined with any other aspect, or portion thereof, described herein, the method further includes at an end of the recorded fluorescence frames, re-computing, via the processor, the starting frame shift and replaying the recorded fluorescence frames.

In a sixteenth aspect of the present disclosure, which may be combined with any other aspect, or portion thereof, described herein, the specified duration is between ten and thirty seconds.

In a seventeenth aspect of the present disclosure, which may be combined with any other aspect, or portion thereof, described herein, the specified duration includes at least two movement peaks of human tissue.

In an eighteenth aspect of the present disclosure, which may be combined with any other aspect, or portion thereof, described herein, the fluorescence image data and the visible light image data include stereoscopic image data.

In a nineteenth aspect of the present disclosure, which may be combined with any other aspect, or portion thereof, described herein, the patient tissue includes at least one of blood vessels, a heart, or lung tissue.

In a twentieth aspect of the present disclosure, which may be combined with any other aspect, or portion thereof, described herein, the first scalar gradients are determined by creating, via the processor, a difference image between the subsequent frames of the fluorescence image data, and summing, via the processor, values of the pixels of the difference image.

In a twenty-first aspect, any of the features, functionality and alternatives described in connection with any one or more of FIGS. 1 to 13 may be combined with any of the features, functionality and alternatives described in connection with any other of FIGS. 1 to 13.

In light of the present disclosure and the above aspects, it is therefore an advantage of the present disclosure to provide a surgical visualization system that eliminates offsets between overlaid images of rhythmically moving tissue.

It is another advantage of the present disclosure to use scalar gradients of images to temporally align recorded fluorescence video data with live or near-live visible light video data.

Additional features and advantages are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein and it is expressly contemplated to claim individual advantageous embodiments separately. Moreover, it should be noted that the language used in the specification has been selected principally for readability and instructional purposes, and not to limit the scope of the inventive subject matter.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION

An apparatus, method, and system are disclosed that provide synchronization between fluorescence image data and visible light image data for tissue that moves with known regularity. The example apparatus, method, and system are configured to provide synchronization by detecting how an image changes between frames. The image change corresponds to detecting the regular and predictable movement of human tissue, such as pulsing of a blood vessel. In particular, peaks or maximum extents of tissue movement is tracked overtime to determine an estimation of the regular periodic movement.

Additionally, the apparatus, method, and system are configured to record a defined time duration of image data in a fluorescence imaging mode. The time duration is defined to include at least two peaks or maximum extents of tissue movement. The example apparatus, method, and system then overlay the recorded fluorescence image data over the live visible light image data such that the peaks or tissue movement extents of the fluorescence image data are aligned with detected peaks or movement extents of the live visible light image data. The frame rate of the fluorescence image data is adjusted to ensure close or almost exact alignment of tissue position shown in both the fluorescence image data and the visible light image data. The example apparatus, method, and system accordingly provide a fluorescence image overlay on visible light images for tissue that has regular movement patterns.

Figure 1:
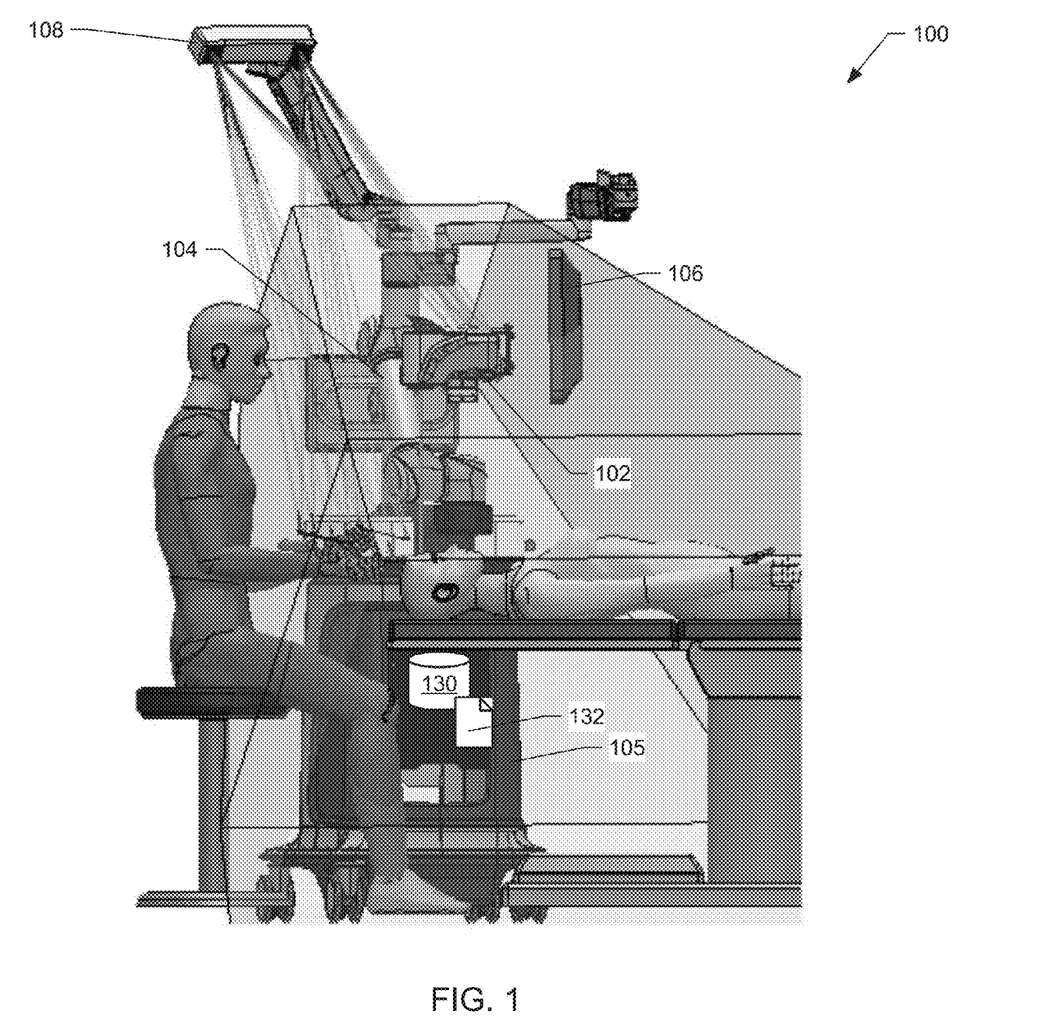
FIG. 1 is a diagram of a surgical visualization system that includes an imaging camera connected to a robotic arm, according to an example embodiment of the present disclosure.

FIG. 1 is a diagram of a surgical visualization system 100 that includes an imaging camera 102 connected to a robotic arm 104, according to an example embodiment of the present disclosure. The imaging camera 102 may include a stereoscopic camera having left and right image sensors. The imaging camera 102 includes one or more lighting sources including a visible light source, a near-infrared ("NIR") light source, and a near-ultraviolet ("NUV") light source. The imaging camera 102 also includes a filter assembly that can accommodate different optical filter pairs. For example, the filter assembly can include an infrared cut filter, a near-infrared bandpass filter, and a near-ultraviolet cut filter. The different filter types are selected to work with different spectra of the light sources and the reflectivity and transmissivity characteristics of a deflecting element to pass certain desired wavelengths of light at predetermined times. Synchronization between the light sources and the filter may be performed by a controller and/or a processor 105 of the imaging camera 102. In some examples, each of the light sources may be provided by a single LED, two LEDs, three LEDs, etc. The NUV light source may include, for example, three 405 nm LEDs.

The imaging camera 102 may have different imaging modes, including a visible light mode, a NIR mode and a NUV mode. For the NIR mode, the camera 102 activates the NIR light source and/or the visible light source. The controller and/or the processor 105 may also deactivate the other light sources. In addition to activating the NIR light source, the controller and/or the processor 105 cause the filter assembly to cause a near-infrared bandpass filter to be placed in the left and right optical paths.

In an example, excitation light transmits through an excitation filter that is configured to remove a large percentage or portion of the excitation light that is within the same wavelength range as that of the emissions filter of the filter assembly. In other words, the excitation filter permits light between, for example 730 nanometers ("nm") to 820 nm (or 738 nm to 802 nm) to pass, corresponding to the absorption wavelength range of ICG, while blocking light having wavelengths above 802 nm or 820 nm (and below 730 nm in some embodiments) to prevent contamination with excitation light having a wavelength above 820 nm. As such, any excitation light that propagates to the end of the optical path due to reflections in the main objective assembly (or from a target surgical site) is blocked by the excitation filter (e.g., the near-infrared bandpass filter) of the filter assembly so that only ICG emissions light (e.g., light having a wavelength between 817 nm to 900 nm) is received at the image sensors.

In some embodiments, the imaging camera 102 is configured to provide back-illumination using visible light while visualizing ICG emission light. In known conventional microscopes, when a surgeon is viewing ICG emission light, the surrounding areas that are not emitting light are completely dark, making it very difficult for the surgeon to introduce or move their instrument at the target surgical site. The imaging camera 102 may switch between the visible light source and the NIR light source while having the near-infrared bandpass filter of the filter assembly engaged with the optical paths. The imaging camera 102 may alternatively activate the visible light source at the same time as the NIR light source. While the light sources are activated, the image sensors record the ICG emission light for stereoscopic display. In this manner, the addition of the visible spectrum light enables the controller and/or a processor 105 to overlay images with better correspondence.

It should be appreciated that the image sensors of the imaging camera 102 have a greater resolution than IR-specific cameras used as accessories in conventional microscopes. The greater resolution of the image sensors produces sharper images with more overall detail. Further, the use of left and right image sensors provides three-dimensional images with depth, which enables a surgeon to safely maneuver instruments in the surgical area while viewing the three-dimensional video on a display monitor 106. The use of single left and right optical paths eliminates the need for optical splitters of known microscopes, thereby decreasing system complexity, cost, and light loss. The maximization of light throughput to the image sensors enables the imaging camera 102 to use less powerful illumination (e.g., 20 to 25 watts) compared to known microscopes, which use up to 400 watts and need to operate at 80% to 100% for proper fluorescence. The use of less light (and power generally) generates less heat at the surgical site, thereby reducing the risk of burning or overheating patient tissue, which reduces the amount of external hydration that needs to be applied to the surgical site.

For an NUV mode, the controller and/or the processor 105 receives the request for the NUV mode and activates the NUV light source. The input may be received from an input device connected to the camera 102 or an input device communicatively coupled to the controller and/or a processor 105. The controller and/or the processor 105 may also deactivate the other light sources. In addition to activating the NUV light source, the controller and/or the processor 105 cause the filter assembly to cause near-ultraviolet cut filters to be placed in the left and right optical paths.

Excitation light transmits through an excitation filter that is configured to remove a large percentage or portion of the excitation light that is within the same wavelength range as that of the near-ultraviolet cut filters of the filter assembly. In other words, the excitation filter permits light between, for example 300 nm-450 nm (or 380 nm to 450 nm) to pass, corresponding to the peak absorption wavelength range of 5-ALA, while blocking light having wavelengths above 450 nm (and below 380 nm in some embodiments) to prevent contamination with excitation light having a wavelength above 480 nm (e.g., light having a peak emission wavelength of 635 nm). As such, any excitation light that makes its way towards the end of the optical path due to reflections in the main objective assembly (or from a target surgical site) is blocked by the excitation filter (e.g., the near-ultraviolet cut filter) of the filter assembly so that only 5-ALA emissions light is received at the image sensors.

As described in more detail below, the controller and/or the processor 105 is configured to synchronize and overlay fluorescence image data with visible light image data. The combined image data is displayed on the display monitor 106. The displayed image may be a stereoscopic image.

FIG. 1 also shows that the system 100 may include a localizer 108 that tracks a position/orientation of the camera 102 relative to a patient. The localizer 108 may also be attached to the robotic arm 104 and is used for registering a field of view of the camera 102 to patient coordinates so that instructions to move the robotic arm 104 or camera 102 are interpreted from the field of view of the patient rather than an absolute position of the system. For example, a surgeon watching the display monitor 106 may select to move the camera left, relative to the displayed image. The controller and/or the processor 105 determines transformations between the displayed image and the position of the robotic arm 104 and/or camera 102 to cause the camera 102 to be moved left with respect to the field of view.

Example Synchronization Procedure

Figure 2:
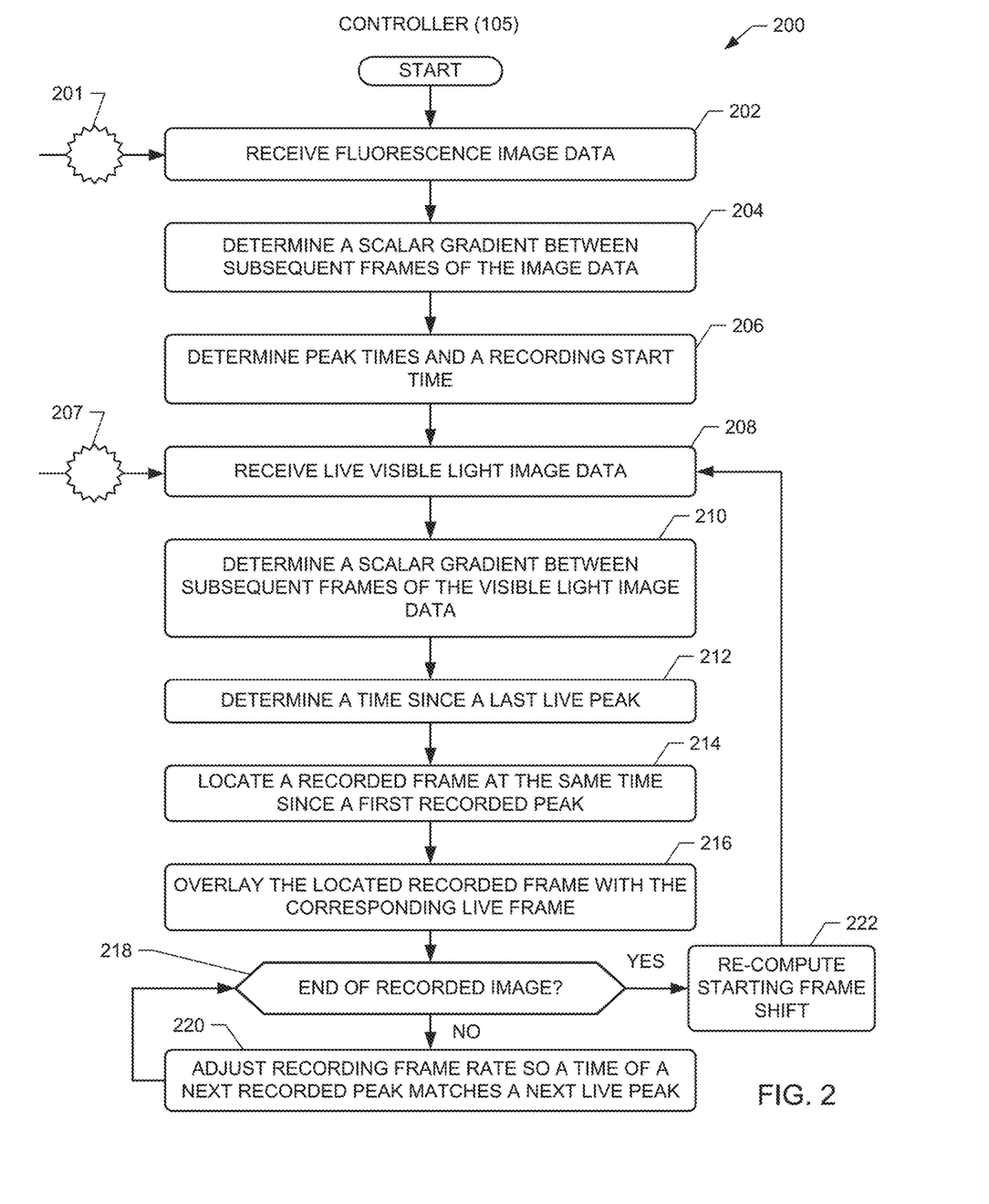
FIG. 2 is a diagram of an example procedure to synchronize live visible light image data with recorded fluorescence image data, according to an example embodiment of the present disclosure.

FIG. 2 is a diagram of an example procedure 200 to synchronize live visible light image data with recorded fluorescence image data, according to an example embodiment of the present disclosure. The example procedure 200 may be carried out by the controller and/or processor 105 of FIG. 1. The example procedure 200 may be specified by one or more instructions 132 (e.g., an algorithm) that are stored on a memory device 130, which is in communication with the controller and/or processor 105. Execution of the instructions 132 by the controller and/or processor 105 cause the controller and/or processor 105 to perform the operations described herein. In some embodiments, the operations of the procedure 200 may be amended based on a configuration of the camera 102 or fluorescence modality of the controller and/or processor 105.

The example procedure 200 begins when the controller 105 places the imaging camera 102 into a fluorescence imaging mode and records fluorescence image data 201 (block 202). The fluorescence image data 201 may have a time duration between 2 seconds to 1 minute, preferably between 20 to 30 seconds. The fluorescence image data 201 includes at least two peaks of repetitive tissue movement of a target surgical site.

Figure 3:
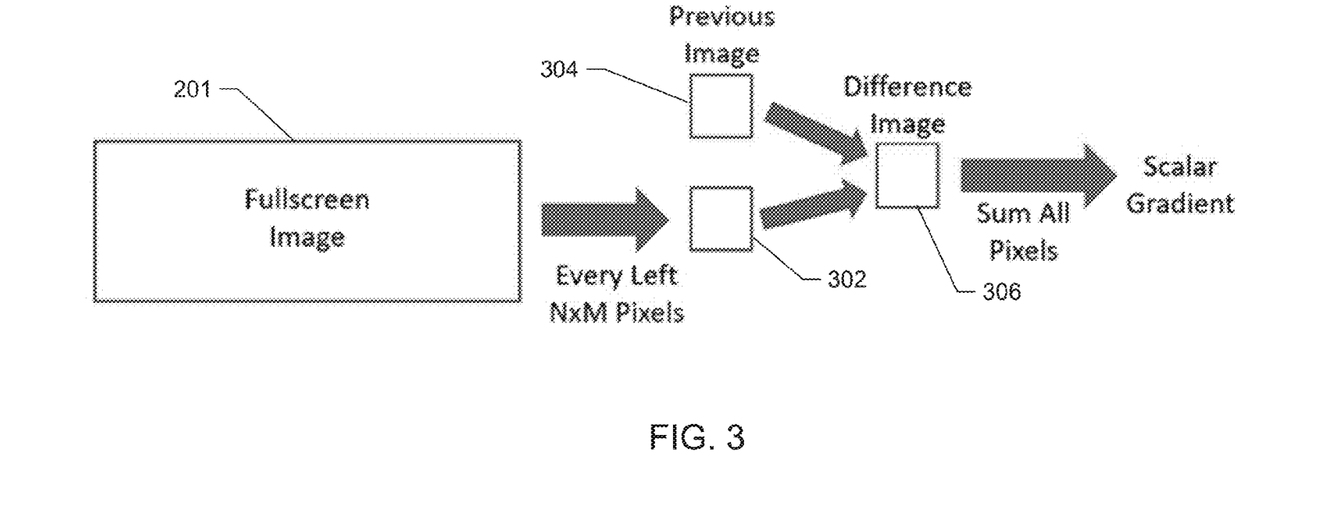
FIG. 3 is a diagram that illustrates how a scalar gradient is determined between two images or frames of video data, according to an example embodiment of the present disclosure.

The example controller 105 next determines a scalar gradient between subsequent frames of the fluorescence image data (block 204). FIG. 3 is a diagram that illustrates how a scalar gradient is determined between two images or frames of video data, according to an example embodiment of the present disclosure. The gradient measures the degree to which the image has changed from the previous image. In this example, the gradient is analyzed from each image to the next to determine when a heartbeat has occurred, namely, when the image is changing most rapidly. When the heart is not beating, the image appears consistent from one image to the next. However, when heart is actively pumping, blood is forced through the vessels causing repeating spasmodic movement in the image.

As shown, the image data 201 originally includes a full screen image that corresponds to a recordable area of a left or right image sensor of the camera 102. Since the algorithm 132 executed by the controller 105 is configured to determine these periods of movement, the small details of the differences from image to image are not needed. In addition, the algorithm 132 executes very efficiently so it can keep pace with the rate of incoming images. Thus, only a subset of an image is required. As shown in FIG. 3, the incoming image 201 is a stereo image, with includes the left and right halves of the image displaying the view from the left and right camera sensors. Since both sides would notice the same image changes, only the left side image is used. In other embodiments, the right side image may be used or both the left and right images may be used. Furthermore, the image size is reduced by a factor of four (for example) both horizontally and vertically to create a smaller version of the image 302. This smaller version of the image 302 still shows a representative difference with a similar reduction of a previous image 304.

The scaling is performed by dividing up the image 201 into a grid where each grid cell contains a 4×4 (for example) array of pixels. These 16 pixels are averaged (thereby reducing the image size by a factor of 16), with the final average pixel value being used in the reduced image 302. Thus, from an original stereo image of 3840×1080, with the left side image size being 1920×1080, the scaled image is of a size of 480×270. Each pixel of the scaled image only stores the red component from the original red, green, and blue pixel components, again, because this channel alone can be used to recognize the rapid image changes of the heartbeats or other tissue. In other embodiments, the blue and/or green pixels are used.

To compute the gradient from one image to the next, the computation needs the current scaled image 302 as well as the previous scaled image 304. A gradient is not computed for the initial image. It is just scaled and copied so it is available for computation with the next frame. All succeeding images are then scaled down by this procedure, then compared with the copied scaled image from the previous image. The comparison is performed for each pixel by subtracting the pixel value from the previous scaled image from the corresponding pixel value in the current scaled image. In some instances, if the pixel difference is greater than a minimum value, the difference may be set to a value of 255, for example. The absolute value of the pixel difference is stored as the pixel value in a third image 306, the difference image of FIG. 3. Finally, all the pixel values for the whole difference frame 306 are summed. The final sum is the scalar gradient.

The method of computing the gradient by summing the pixel differences from one frame to another frame may result in misleading determinations of the heartbeat pulse if the camera or scene being viewed is jiggled. To reduce this error, an assumption is made that the heartbeat is relatively regular. Any rapid change in gradient arriving less than 90% to the time of the next expected heartbeat is ignored. A more robust alternative can also be used, that of summing the pixels in the scaled images and computing the gradient as the difference between these two sums. This would have the effect of allowing parts of the scene to change their position within the image, but still sum to the same or similar value from frame to frame.

Figure 4:
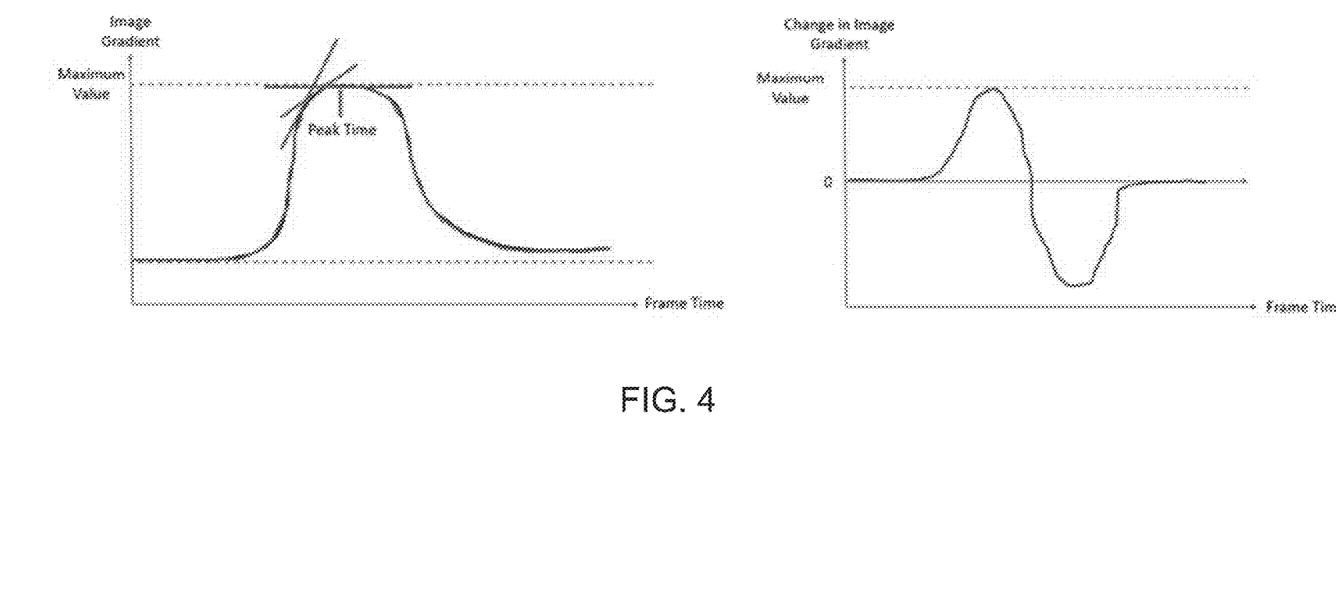
FIG. 4 is a diagram of graphs that shows how a scalar gradient changes over time for images corresponding to one heartbeat, according to an example embodiment of the present disclosure.

FIG. 4 is a diagram of graphs that show how a scalar gradient changes over time for images corresponding to one heartbeat. As shown, during heartbeat expansion, there is a strong positive change in image gradient. Similarly, during heartbeat retraction, there is a strong negative change in image gradient. A summation of the image gradients over the time for the heartbeat shows a peak time at or right after maximum vessel expansion, which then reduces as the vessel relaxes.

Figure 5:
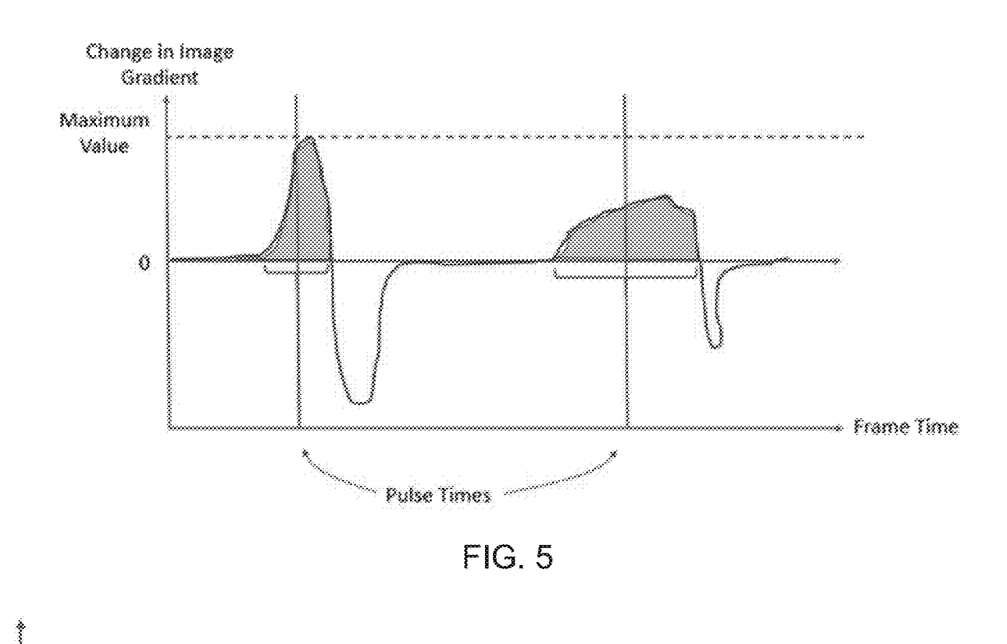
FIG. 5 is a graph that shows gradient peaks may vary widely, according to an example embodiment of the present disclosure.

FIG. 5 is a graph that shows gradient peaks may vary widely. In these instances, the controller 105 may accumulate an area of positive slope and use the midpoint in time for calculating or averaging the gradient.

Figure 6:
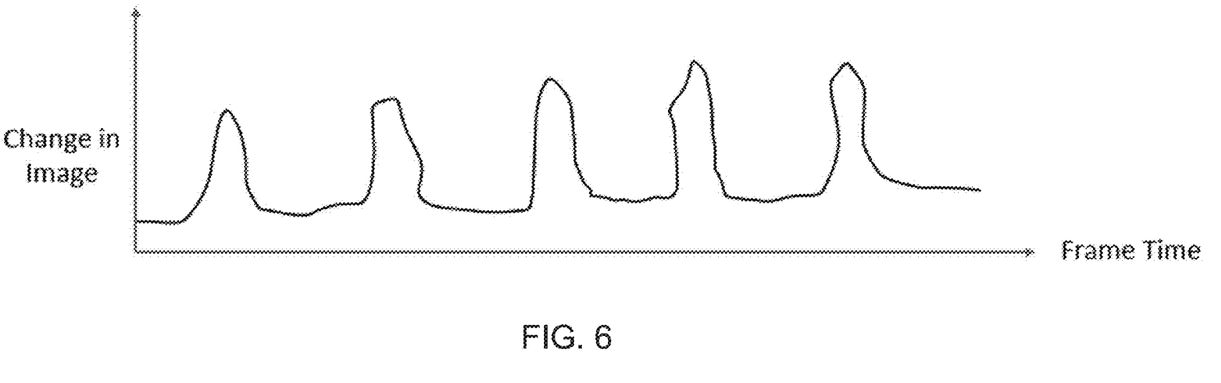
FIG. 6 is a diagram of a scalar gradient over time for a recorded video clip of fluorescence image data, according to an example embodiment of the present disclosure.

FIG. 6 is a diagram of a scalar gradient over time for a recorded video clip of fluorescence image data 201, according to an example embodiment of the present disclosure. As shown, the peaks correspond to times where the blood vessel is at a maximum expansion or movement, and corresponds roughly to a heartbeat.

Figure 7:
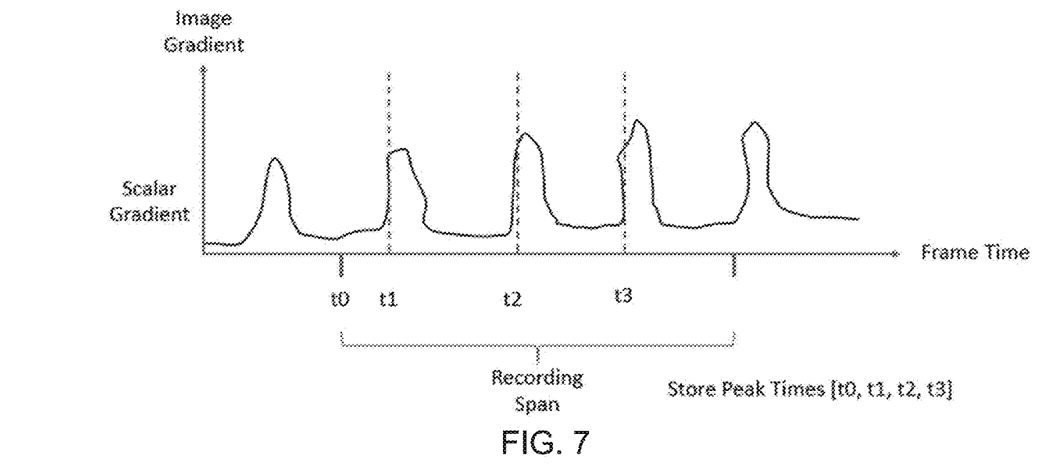
FIG. 7 shows an example of identifying the peak times and a recording span, according to an example embodiment of the present disclosure.
Figure 8:
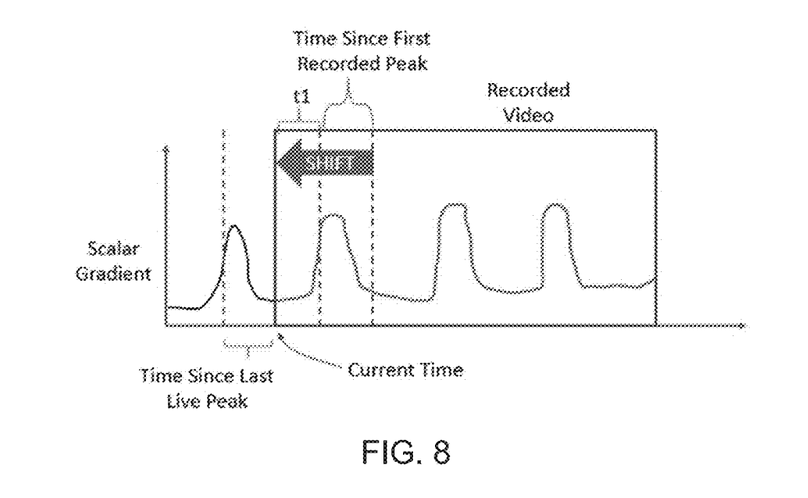
FIG. 8 is a diagram that shows the alignment of a last recorded peak and a live peak for synchronizing live visible light frames and recorded fluorescence frames, according to an example embodiment of the present disclosure.

Returning to FIG. 2, the controller 105 next determines peak times and a recording start time for the fluorescence image data 201 (block 206). FIG. 7 shows an example of the controller 105 identifying the peak times. The controller 105 uses the peak times to determine a recording span. The controller 105 is then ready to apply the selected fluorescence image data 201 to live visible light image data. Next, the controller 105 receives the live visible light image data 207 (block 208). Using the method discussed above in connection with block 204 and FIGS. 3 to 7, the controller 105 determines a scalar gradient between subsequent frames of the visible light image data 207 (block 210). The controller 105 then determines a time since a last live peak of the live image data 207 (block 212). Further, the controller 105 locates a recorded frame at a same time since a first recorded peak (block 214). As shown in FIG. 8, the controller 105 uses the time since both the last recorded peak and live peak to align the live visible light frame and the fluorescence frame. In other words, the controller 105 sets the first playback frame of the recorded image data to this determined frame of the live video data using time since a last peak to provide time-based frame alignment. Once the frames are synchronized, the controller 105 overlays the fluorescence frame over the visible light frame for display by the monitor 106 (block 216).

In some embodiments, the controller 105 may segment the fluorescence image data to include only sections that include fluorescence. In these embodiments, the controller 105 applies the segmented portions of the image data or frames over the live visible light image data. The controller 105, in some embodiments, may segment the fluorescence image data prior to determining the scalar gradients.

Figure 9:
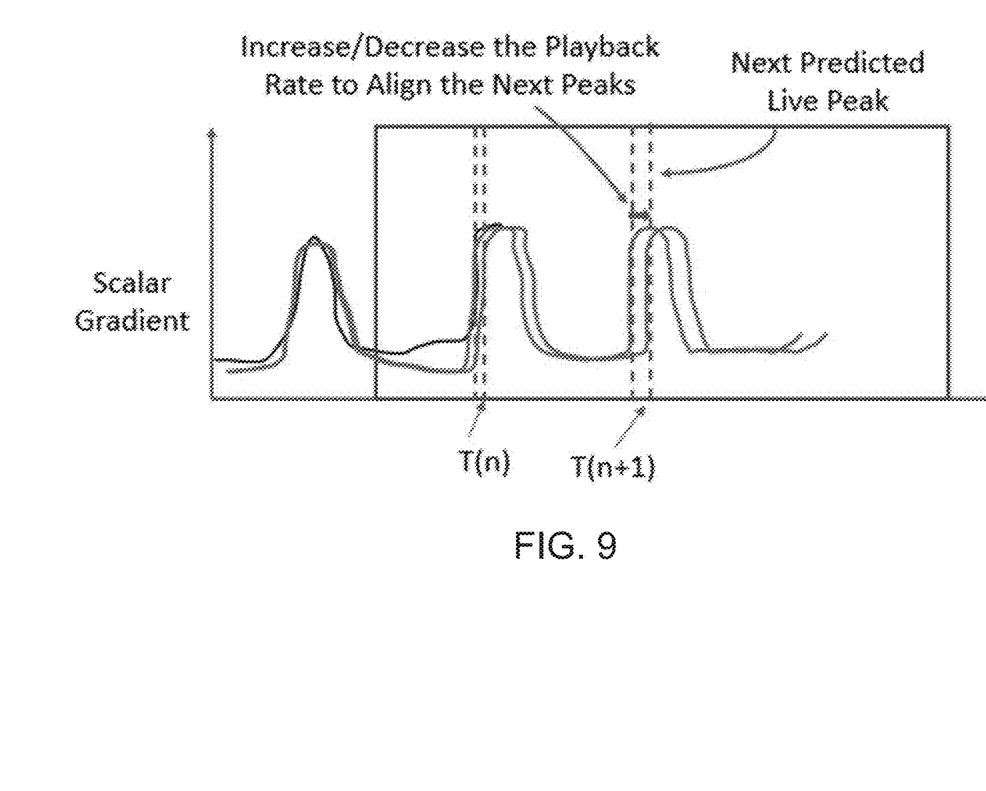
FIG. 9 is a diagram that shows an adjustment of a frame rate of a recording so the time of the next peak matches the next live peak, according to an example embodiment of the present disclosure.

As shown in FIG. 2, after one or more frames of the fluorescence recorded image data are overlaid on the visible light image data, the controller 105 determines if the fluorescence frames correspond to an end of the recording (block 218). If it is not the end of the recording, the controller 105 computes a running average of time between peaks in a live image stream and adjusts a frame rate of the recording so the time of the next peak matches the next live peak, as shown in FIG. 9 (block 220). At the next live peak, the controller 105 adjusts the frame rate again based on the current recording frame and continues until the end of the recording. The controller 105 may ignore live peaks that are less than 90% of the expected live peak time span. As shown in FIG. 2, at the end of the recording, the controller 105 re-computes the starting frame shift (block 222) and returns to block 208 for newly received visible light image data. In this manner, the recorded fluorescence image data is repeated multiple times. It should be appreciated that the image reduction and gradient calculation can be performed in less than 0.4 milliseconds ("ms") to provide for smooth video streaming. Further, the time to compute the frame rate adjustment for the recorded fluorescence recording is negligible or less than 5 ms.

Thus, the controller 105 uses the image gradients to align the timing playback of the fluorescence image data superimposed on the live or near-live visible light image data. The fluorescence image data may correspond to a sufficient number of frames to capture one, two, three, etc. cycles of tissue movement. Thus, the recorded fluorescence image data constitutes a short video that is continuously replayed over the live or near-live visible light image data.

In some instances, the controller 105 may periodically (e.g., every five minutes, ten minutes, etc.) record new fluorescence image data. Further, the controller 105 may detect camera movement and/or a change in magnification or focal point and record new fluorescence image data to correspond to the changed field of view.

Figure 10:
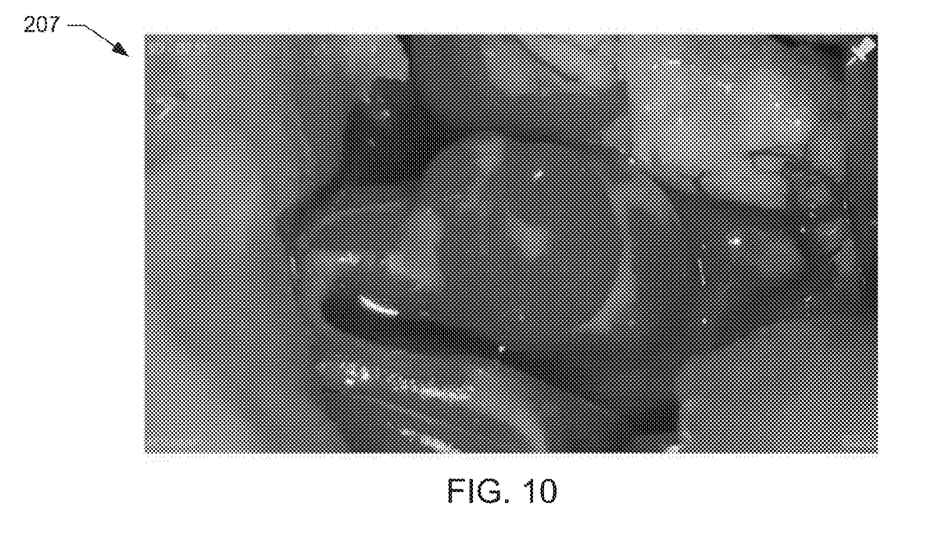
FIG. 10 is an image of visible light image data, according to an example embodiment of the present disclosure.
Figure 11:
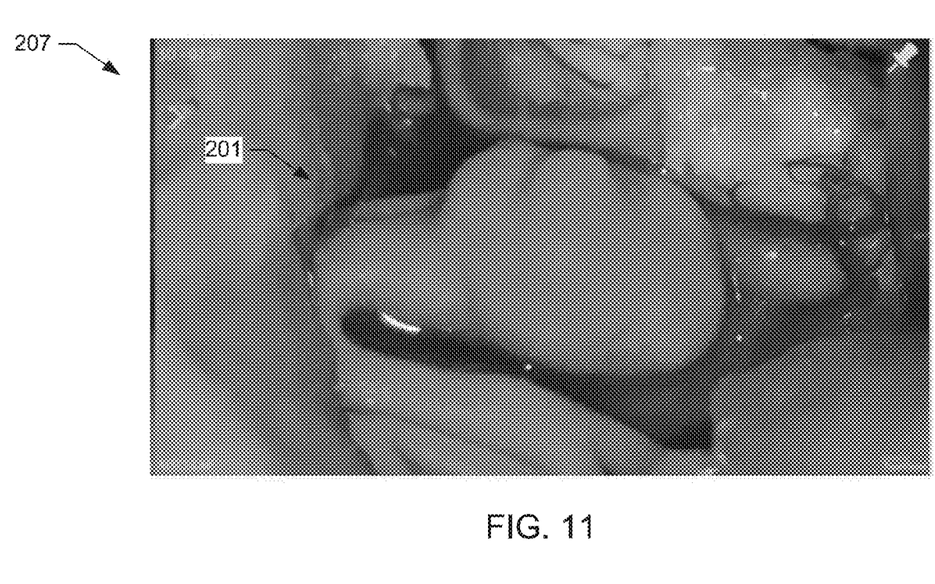
FIG. 11 is a diagram with the fluorescence image data overlaid on the visible light image data, according to an example embodiment of the present disclosure.

FIG. 10 is an image of visible light image data (e.g., a visible light frame 207). The image 207 includes a blood vessel of a patient's brain. The vessel projects slightly in a rhythmic pattern based on the patient's heartbeat. FIG. 11 is a diagram with at least a portion of the fluorescence image data 201 overlaid on the visible light image data 207. As shown, certain tissue emits fluorescent light. The controller 105 segments or otherwise selects a portion of the florescence image data 201 that corresponds to fluorescence emission, provides coloration to enhance user viewing, and overlays the portion of the image 201 on the visible light image 207.

Figure 12:
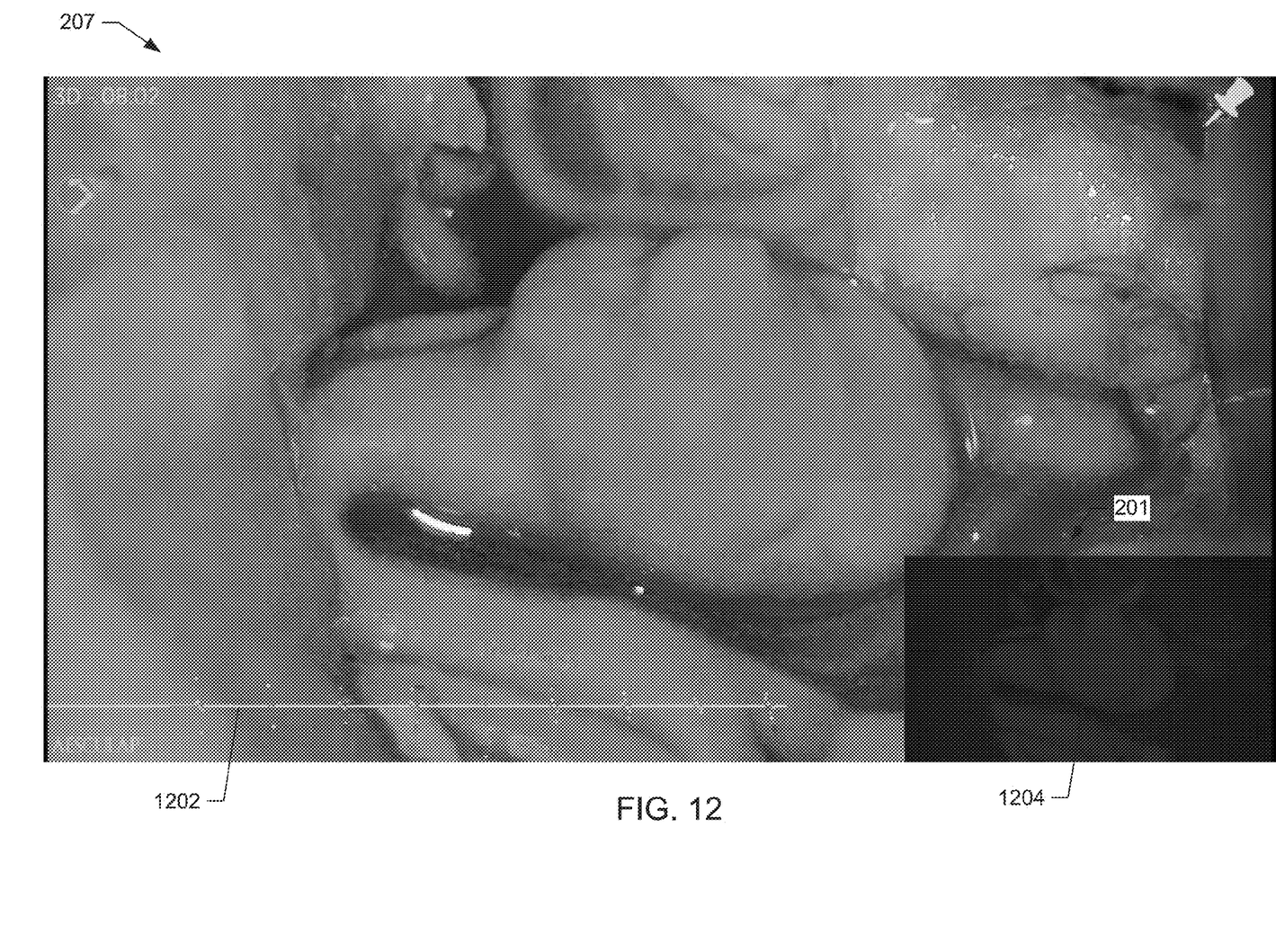
FIG. 12 is a diagram that shows the overlay with respect to tissue movement, according to an example embodiment of the present disclosure.
Figure 13:
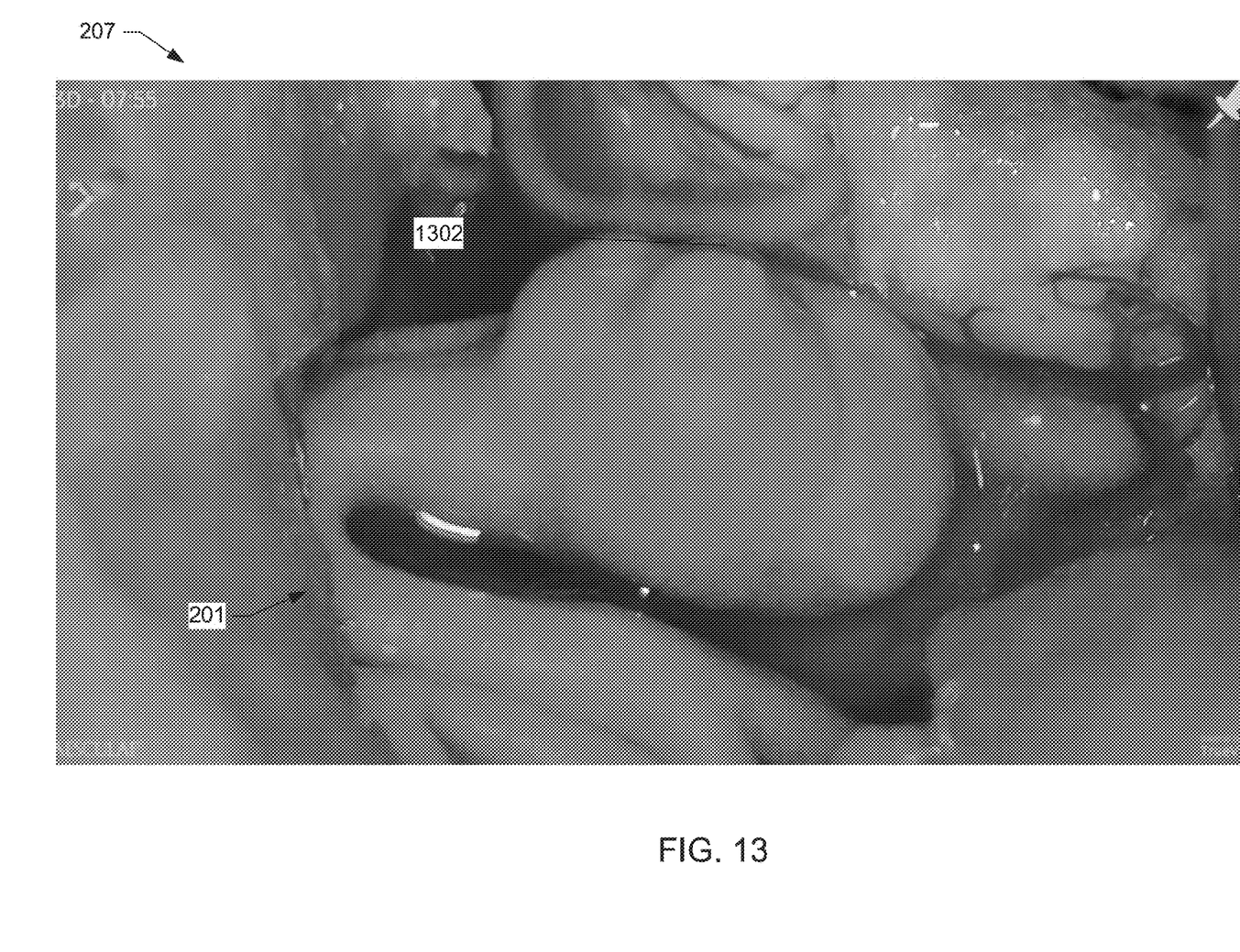
FIG. 13 shows a comparison where there is no synchronization between the visible light and fluorescence image data.

FIG. 12 shows the overlay with respect to tissue movement. A line 1202 indicates the detected peaks of tissue movement. An insert 1204 shows the recorded fluorescence image data 201 that is applied to the live visible light image data 207 to produce the image shown. The fluorescence of the tissue matches the movement. By comparison, FIG. 13 shows a comparison where there is no synchronization between the visible light 207 and fluorescence image data 201. Without synchronization there is an offset 1302 of the fluorescence image data from the visible light image data, which can be distracting or problematic for surgeons. The methods, apparatus, and system discloses herein accordingly eliminates this offset 1302, thereby improving the overlay of fluorescence images on visible light images.

CONCLUSION

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A surgical imaging apparatus configured to:
receive fluorescence image data of patient tissue from a camera, the fluorescence image data having a specified duration;
determine first scalar gradients between subsequent frames of the fluorescence image data;
determine, as recorded fluorescence frames, peak times and a recording start time of the fluorescence image data using the determined scalar gradients plotted over a recording time;
receive live visible light image data;
determine second scalar gradients between subsequent frames of the visible light image data;
determine, as an overlay time, a time since a last peak of the visible light image data using the determined second scalar gradients;
locate a frame of the recorded fluorescence frames that has a same overlay time since a first recorded peak;
create an overlay image by overlaying or superimposing at least a portion of the located frame of the recorded fluorescence frames on a corresponding frame of the visible light image data; and
cause the overlay image to be displayed,
wherein the specified duration is between ten and thirty seconds, and
wherein the specified duration includes at least two movement peaks of human tissue.

2. The apparatus of claim 1, wherein the apparatus is further configured to:
compute a running average time between peaks in the live visible light image data; and
adjust a recording frame rate of the recorded fluorescence frames so that a next recorded peak matches a next live peak.

3. The apparatus of claim 2, wherein the apparatus is further configured to at an end of the recorded fluorescence frames, re-compute a starting frame shift and replay the recorded fluorescence frames.

4. The apparatus of claim 1, wherein the fluorescence image data and the visible light image data include stereoscopic image data.

5. The apparatus of claim 1, wherein the patient tissue includes at least one of blood vessels, a heart, or lung tissue.

6. The apparatus of claim 1, wherein the first scalar gradients are determined by:
creating a difference image between the subsequent frames of the fluorescence image data; and
summing values of pixels of the difference image.

7. The apparatus of claim 6, wherein the subsequent frames are scaled down by at least a factor of four before the difference image is created.

8. The apparatus of claim 1, wherein the second scalar gradients are determined by:
creating a difference image between the subsequent frames of the visible light image data; and
summing values of pixels of the difference image.

9. The apparatus of claim 1, wherein the apparatus is further configured to:
detect or receive an indication of camera movement;
receive new fluorescence image data comprising fluorescence frames of the patient tissue from the camera, the new fluorescence image data having the specified duration;
responsive to detecting or receiving the indication of the camera movement, determine new first scalar gradients between subsequent frames of the new fluorescence image data;
locate a new frame of the new recorded fluorescence frames that has a same overlay time since a new first recorded peak;
create a new overlay image by overlaying or superimposing at least a portion of the new located frame of the new recorded fluorescence frames on the corresponding frame of newly received visible light image data; and
cause the new overlay image to be displayed.

10. A surgical imaging apparatus configured to:
receive fluorescence image data of patient tissue from a camera, the fluorescence image data having a specified duration;
determine first scalar gradients between subsequent frames of the fluorescence image data;
determine, as recorded fluorescence frames, peak times and a recording start time of the fluorescence image data using the determined scalar gradients plotted over a recording time;
receive live visible light image data;
determine second scalar gradients between subsequent frames of the visible light image data;
determine, as an overlay time, a time since a last peak of the visible light image data using the determined second scalar gradients;
locate a frame of the recorded fluorescence frames that has a same overlay time since a first recorded peak;
create an overlay image by overlaying or superimposing at least a portion of the located frame of the recorded fluorescence frames on a corresponding frame of the visible light image data; and
cause the overlay image to be displayed,
wherein the fluorescence image data and the visible light image data include stereoscopic image data, and
wherein the patient tissue includes at least one of blood vessels, a heart, or lung tissue.

11. The apparatus of claim 10, wherein the apparatus is further configured to:
compute a running average time between peaks in the live visible light image data; and
adjust a recording frame rate of the recorded fluorescence frames so that a next recorded peak matches a next live peak.

12. The apparatus of claim 11, wherein the apparatus is further configured to at an end of the recorded fluorescence frames, re-compute a starting frame shift and replay the recorded fluorescence frames.

13. The apparatus of claim 10, wherein the specified duration is between ten and thirty seconds.

14. The apparatus of claim 10, wherein the specified duration includes at least two movement peaks of human tissue.

15. The apparatus of claim 10, wherein the second scalar gradients are determined by:
creating a difference image between the subsequent frames of the visible light image data; and
summing values of pixels of the difference image.

16. A surgical imaging apparatus configured to:
receive fluorescence image data of patient tissue from a camera, the fluorescence image data having a specified duration;
determine first scalar gradients between subsequent frames of the fluorescence image data;
determine, as recorded fluorescence frames, peak times and a recording start time of the fluorescence image data using the determined scalar gradients plotted over a recording time;
receive live visible light image data;
determine second scalar gradients between subsequent frames of the visible light image data;
determine, as an overlay time, a time since a last peak of the visible light image data using the determined second scalar gradients;
locate a frame of the recorded fluorescence frames that has a same overlay time since a first recorded peak;
create an overlay image by overlaying or superimposing at least a portion of the located frame of the recorded fluorescence frames on a corresponding frame of the visible light image data; and
cause the overlay image to be displayed,
wherein the first scalar gradients are determined by:
creating a difference image between the subsequent frames of the fluorescence image data, and
summing values of the pixels of difference image, and
wherein the subsequent frames are scaled down by at least a factor of four before the difference image is created.

17. The apparatus of claim 16, wherein the apparatus is further configured to:
compute a running average time between peaks in the live visible light image data; and
adjust a recording frame rate of the recorded fluorescence frames so that a next recorded peak matches a next live peak.

18. The apparatus of claim 17, wherein the apparatus is further configured to at an end of the recorded fluorescence frames, re-compute the starting frame shift and replay the recorded fluorescence frames.

19. The apparatus of claim 16, wherein the specified duration is between ten and thirty seconds.

20. The apparatus of claim 16, wherein the specified duration includes at least two movement peaks of human tissue.

* * * * *